United States Patent [19]
Mulzet et al.

[11] 3,978,992
[45] Sept. 7, 1976

[54] POSITIONING APPARATUS

[75] Inventors: Alfred Paul Mulzet, Endicott; James Louis Sirico, Vestal, both of N.Y.

[73] Assignee: International Business Machines Corporation, Armonk, N.Y.

[22] Filed: July 2, 1975

[21] Appl. No.: 592,584

[52] U.S. Cl. .............................. 214/1 BB; 198/794; 214/1 BA
[51] Int. Cl.² ........................................ B65G 25/00
[58] Field of Search ................ 214/1 BB, 1 BT, 1 B, 214/1 BA, 1 BS; 198/179, 218

[56] References Cited
UNITED STATES PATENTS

| | | | |
|---|---|---|---|
| 3,115,966 | 12/1963 | Leiter | 198/103 |
| 3,233,751 | 2/1966 | Bannon | 214/1 BB |

FOREIGN PATENTS OR APPLICATIONS

| | | | |
|---|---|---|---|
| 343,274 | 1/1960 | Switzerland | 214/1 BB |
| 1,035,896 | 7/1966 | United Kingdom | 214/1 B |

*Primary Examiner*—Frank E. Werner
*Attorney, Agent, or Firm*—Norman R. Bardales

[57] ABSTRACT

Positioning apparatus is disclosed which positions an object with respect to two predetermined lateral positions. In addition, the object is indexable by the apparatus in a step-by-step manner in an incidental direction with respect to each of the two lateral positions. It includes an endless sprocket chain entrained about two sprocket wheels. The chain carries a first member which is pivotably connected to the chain. A second member is affixed to the first member and is adapted to support the object. The second member is slidably mounted to a movable third member which in turn is guided by guiding means such as rails that guides the third member means in a predetermined aligned relationship with the reaches of the chain. In addition, chain guide means guide the chain along the first and second reaches. Driver means are coupled to one of the sprocket wheels to drive the endless chain. In response to the movement of the chain, the first member is capable of movement to and along each of the chain's first and second, i.e., two, reaches. The object in turn is thus positionable with respect to the first and second positions when the chain carries the first member along the first and second reaches, respectively. In the preferred mode of operation, the chain is driven in one direction to move the object from the first position to the second position and in the reverse direction when the object is returned from the second position to the first position.

21 Claims, 6 Drawing Figures

POSITIONING APPARATUS

BACKGROUND OF THE INVENTION

1. Field of the Invention

This invention is related to positioning apparatus and, more particularly, to positioning apparatus for positioning an object with respect to two lateral positions.

2. Description of the Prior Art

In certain applications, it is often desirous to position an object with respect to two spaced positions. These applications include, for example, article handling devices such as inspection or other type probe devices, drills, workpiece carriers, etc., and the like.

One particular application, for example, known in the prior art is an automatic sample testing machine used for testing radioactive samples, which are contained in test tubes, within the well of a well-type scintillation counter. This prior art machine employs conveyor means which positions a test tube gripper assembly or mechanism from a test tube gripper station to the scintillation counter well station and back. The conveyor means includes a twin pair of endless sprocket chains substantially aligned in parallel vertical planes. Each chain is entrained about a set of five sprocket wheels such that each chain is provided with a pentagonal-like configuration with elongated reached or sides between the sprocket. Corresponding sprockets of the two sets are aligned with each other so that the two chains have identical aligned configurations.

The positioning apparatus of this prior art machine has a tranversely extended shaft rotatably carried by two brackets, each of which is mounted to one of the two chains. Mounted on the extended shaft is the test tube gripper assembly so that the latter is supported thereby and between the two chains in a straddled manner. The twin chains' composite pentagonal configuration is such that it has two opposing vertical sides, a shorter one of which is associated with the test tube gripper station and the longer one of which is associated with the well station, a top horizontal side connecting the upper ends of the two vertical sides, an opposing somewhat shorter bottom horizontal side which is connected at one end to the lower end of the short vertical side, and an inclined side which connects the other end of the shorter horizontal side to the lower end of the long vertical side.

In operation of the prior art machine, the test tubes are carried on an indexable annular horizontal turntable which indexes the turntable to the gripper station. The superimposed gripper mechanism, when actuated at the gripper station, grips a test tube so that the conveyor means carries it and the tube gripped thereby first vertically upwards along the short vertical side withdrawing the tube from the table carrier, then along the upper horizontal side, and then vertically downward along the long vertical side where the tube is inserted into the scintillation counter well, which in the particular prior art machine, is located below the center opening of the annular turntable. To withdraw the tube from the wall after the test has been completed and return the tube to the carrier turntable, the direction of the twin chain is reversed.

The positioning apparatus of the prior art are complex, and generally unreliable and/or unstable, particularly for applications where positioning of the object is critical. For example, in the prior art machine previously described, the elongated reaches of the chains are subject to sagging which is not fully controllable by tensioning sprockets which are provided for this purpose. As a result, should the test tubes be intentionally or unintentionally loaded to capacity with the specimen, spillage is likely to occur due to swaying of the freely suspended gripper mechanism and/or of the chains caused by the instability of the sagging chains. For similar reasons, the sag in the chains makes accurate positioning of the object at each of the positions unreliable so that the prior art machine is not suitable for applications where accurate positioning is critical. Moreover, in the particular prior art machine aforedescribed, these disadvantages are further compounded by the requirement therein of using two chains, since each chain is susceptible to sagging by different amounts.

SUMMARY OF THE INVENTION

It is an object of this invention to provide object positioning apparatus.

It is another object of this invention to provide object positioning apparatus which is relatively simple, reliable and/or stable.

Still another object of this invention is to provide object positioning apparatus of the aforementioned kind which positions an object to two positions in a highly accurate and precise manner.

Still another object of this invention is to provide object positioning apparatus of the aforementioned kind which is readily adaptable to automatic operation.

Still other objects of this invention are to provide object positioning apparatus which positions an optical inspection probe mechanism to two stations of an automatic testing machine.

Still another object of this invention is to provide object positioning apparatus which positions a test tube gripper mechanism to two stations of an automatic testing machine.

According to one aspect of the invention, there is provided apparatus for positioning an object to two spatially displaced first and second positions. The apparatus includes first and second rotatably sprocket wheels disposed in a common plane. An endless sprocket chain is entrained about the two sprocket wheels in operable relationship. The chain has first and second opposing reaches between the wheels. First member means is pivotably connected to the chain. Second member means is affixed to the first member means and adapted to support the object. Third member means has the second member means slidably mounted thereto. Guide member means are provided for guiding the third member means in a predetermined aligned relationship with the reaches. Also, chain guide means guide the chain along the first and second reaches. Driver means are coupled to one of the wheels to drive the endless chain. In response to movement of the chain, the first member means is capable of movement to and along each of the first and second reaches. The object is positionable by the driver means with respect to the first position when the chain carries the first member means along the first reach. Also, the object is positionable by the driver means with respect to the second position when the chain carries the first member means along the second reach.

The foregoing and other objects, features and advantages of the invention will be apparent from the following more particular description of the preferred embodiments of the invention, as illustrated in the accompanying drawing.

BRIEF DESCRIPTION OF THE DRAWING

In the figures, like elements are designated with similar reference characters.

DESCRIPTION OF THE PREFERRED EMBODIMENTS

Figure 1:
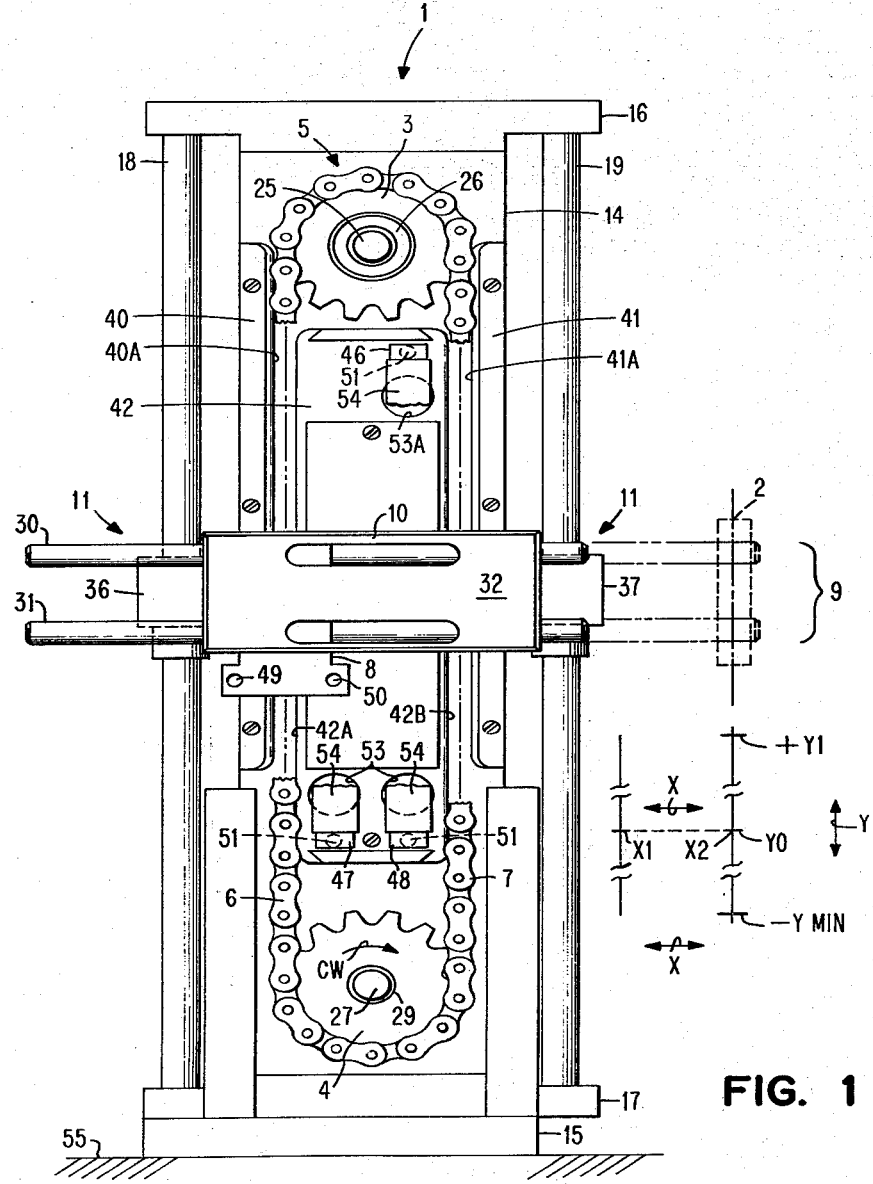
FIG. 1 is a front elevation view of a preferred embodiment of the object positioning apparatus of the present invention.
Figure 2:
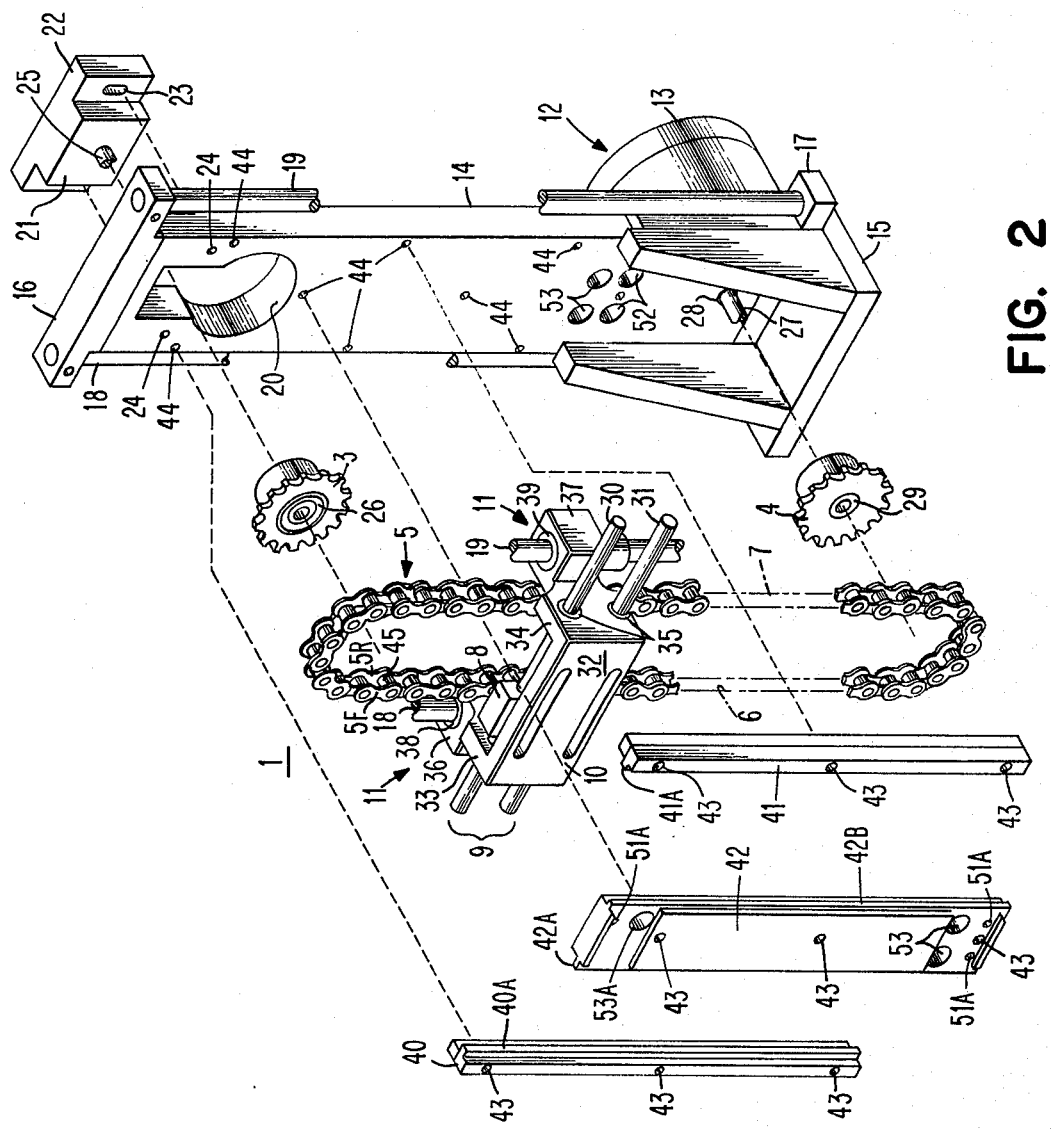
FIG. 2 is an exploded perspective view of the embodiment of FIG. 1.

Apparatus 1 of FIGS. 1, 2 positions object 2 to two spatially displaced first and second positions designated X1 and X2, respectively, in FIG. 1. For sake of clarity, object 2 is shown schematically in outline form in FIG. 1 and is omitted in FIG. 2.

In general, apparatus 1 includes two similar sprocket wheels 3, 4, which are disposed in a common plane. An endless sprocket chain 5 is entrained about wheels 3, 4 in operable relationship. The chain 5 has first and second opposing reaches 6 and 7, which in the preferred embodiment are substantially parallel and elongated reaches, between the wheels 3, 4. First member mean 8 is pivotably, i.e., rotatably, connected to chain 5. Second member means 9 is affixed to first member means 8 and is adapted to support the object 2. Third member means 10 has second member means 9 slidably mounted thereto. Guide member means 11 guides third member means 10 in a predetermined aligned relationship with reaches 6, 7, as hereinafter explained. In the preferred embodiment, means 10 is guided by means 11 in a parallel relationship with reaches 6, 7. Chain guide means 40 – 42 guide chain 5 along the first and second reaches 6, 7.

Driver means, generally indicated by the reference character 12 and which preferably comprises a reversible stepper motor 13, is coupled to wheel 4. Driver means 12 drives the endless chain 5. As a result, first member means 8 is capable of movement to and along each of the reaches 6, 7.

In the preferred embodiment, object 2 is positionable by apparatus 1 with respect to an orthogonal frame of reference having X and Y designated coordinates. Thus, as shown in FIG. 1, object 2 is positionable in the incidental Y direction by driver means 12 with respect to the first position X1 when chain 5 carries first member means 8 along chain reach 6. The object 2 is also positionable in the incidental Y direction by driver means 12 with respect to the second position X2 when chain 5 carries first member means 8 along chain reach 7.

Referring not to FIGS. 1 and 2 in greater detail, an upright platelike center frame member 14 is affixed to a stand 15 by suitable means, not shown, such as screws, bolts or the like. Secured by similar suitable means, not shown, to the upper and lower edges of member 14 are top and bottom T-shaped cap or end frame members 16, 17. Guide member means 11 preferably includes a pair of parallel elongated cylindrical rods 18, 19 which are fitted and secured at their respective ends into mounting holes provided in the cross-bar portions of members 16, 17 for this purpose. Members 16, 17 and rods 18, 19, when assembled, are in symmetrical aligned relationship with the frame member 14. In FIG. 2, rods 18, 19 are shown in partial broken away form with the central portions thereof being shown in guiding relationship with third member means 10, for sake of clarity.

Member 14 is provided with an inverted keyhole-shaped aperture 20. The circular portion of aperture 20 aids in the assembling of the apparatus 1. Fitted in the rectangular portion of aperture 20 is a compatibly rectangularly configured stem portion 21 of T-shaped bracket 22. The bracket 22 is mounted to the rear face of frame 14 by bolts or the like, not shown, which pass through two alignment adjusting elongated openings or slots, e.g., slot 23, located on the two cross bar portions, respectively, of bracket 22 and which are threadably engageable with the holes 24 of member 14. Secured to the base of stem portion 21 is a projecting idler sprocket shaft 25. The shaft 25 is of sufficient length so that when bracket 22 is mounted to frame member 14, it projects sufficiently forward of the front face of member 14 so as to have rotatably mounted thereon sprocket wheel 3 via a suitable bearing, i.e., roller bearing 26. The inner race of bearing 26 is mounted on the stationary shaft 25 and the outer race is affixed to the center of sprocket wheel 3.

Motor 13 is also mounted to the rear face of member 14 by suitable means, not shown. When so mounted, the motor shaft 27 of motor 13 passes through an opening 28 provided in the member 14 for this purpose. The projection of shaft 27 forward of the front face of member 14 is sufficient to have the sprocket wheel 4 mounted to it by an appropriate keyed collar member 29 so that wheel 4 rotates with shaft 27 when the motor 13 is actuated. When assembled, shafts 25 and 27 are in vertical alignment.

Figure 3:
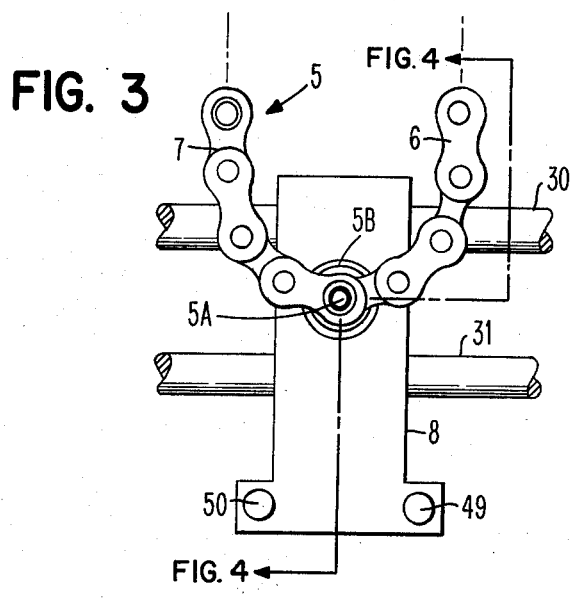
FIG. 3 is an enlarged partial rear elevation view of a certain part of the apparatus of FIG. 1.
Figure 4:
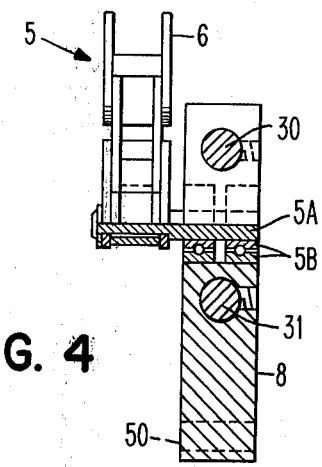
FIG. 4 is a partial cross-sectional view taken along the lines 4—4 of FIG. 3.

First member means 8 is in the form of an inverted rectangular block, cf., FIG. 3. Means 8 is pivotably, i.e., rotatable, mounted to an elongated shaft or pin 5A via bearing 5B, FIG. 4. Shaft 5A is secured to a link of chain 5, and, as shown in FIGS. 3, 4, also acts as one of the link pins for the particular chain link to which it is secured. That is to say, the outer race of bearing 5B is fixed to block 8 and its inner race is rotatable on pin 5A. In FIGS. 3, 4, means 8 is shown at its dead center lowest position on the chain 5, sprocket wheel 4 being omitted in FIGS. 3, 4, for sake of clarity.

Second member means 9 is preferably a pair of parallel elongated cylindrical bars or rods 30, 31, which are affixed to block 8 such as, for example, by a temperature shrink fit process or by other suitable means. In apparatus 1, the coplanar parallel bars 30, 31 are carried by block 8 in parallel relationship with the plane of chain 5 and transverse, i.e., normally incident, to the direction of chain reaches 6, 7.

Third member means 10 includes a U-shaped member having front and two side portions 32 and 33, 34, respectively. Two slide type bushings are provided and housed in each side portion 33, 34, only the two bushings 35 of side 34 being shown in the drawing for sake of clarity. Bars 30 and 31 are slidably mounted in the appropriate ones of the bushings carried by side members 33, 34. Affixed to each of the side portions 33, 34 or made as an integral part thereof is a block 36, 37, respectively, which include or house slide type bushings 38, 39, respectively, and which are slidably mounted to the bars 18, 19, respectively. Thus, means 10 guides the means 9 and, in turn, means 10 is guided by the means 11.

The effect of the combination of means 8 – 11 is to provide very accurate and precise positioning of and/or stability to the object 2 as will become apparent from the operation of the apparatus as described hereinafter.

Chain guide means 40 – 42 are shown as elongated outer guide members 40, 41 and inner elongated guide center member 42. The member 40 has a projecting guide edge 40A which faces the projecting guide edge 42A of member 42. Similarly, member 41 has a projecting guide edge 41A that faces projecting guide edge 42B of member 42. Members 40 – 42 are secured to the front face of member 14 by screws or the like, now shown, which pass through appropriate holes 43 provided in the members 40 – 42 and are threadably engaged with aligned opening 44 provided in member 14. The edge 40A protrudes slightly between the front link plate and rear link plate; see, for example, front plate 5F and rear plate 5R and on the outer side of the chain link pins, e.g., pin 45, of the chain links of chain 5 along the chain reach 6. In a similar manner, the edge 42A protrudes slightly between the front and rear link plates along the reach 6, but is located on the inner side of the chain link pins. The same arrangement occurs with the respective edges 41A, 42B and corresponding chain link parts associated with reach 7. When assembled edges 40A, 41A, 42A, 42B are in substantial parallel and coplanar alignment with parallel reaches 6, 7.

In the preferred embodiment, suitable sensors such as Hall cell devices 46, 47, 48 are employed to provide control signals used in positioning the object 2. For this purpose, a pair of cylindrical actuating permanent magnets 49, 50 are carried by the block 8 to co-act with the cells 46 – 48. Cell 46 is actuated exclusively by magnet 49 and used to provide control signals indicative when the block 8 and, hence, object 2 is in a predetermined home position relative to the X direction. Cells 47 and 48 are actuated exclusively by magnets 50 and 49, respectively, and are used to provide control signals when the block 8 and, hence, object 2 is indexed to a predetermined Y position with respect to position X1 and X2, respectively, as explained in greater detail hereinafter. For sake of clarity, cells 46 – 48 are omitted in FIG. 2.

The cells 46 – 48 are planar in configuration and have appended normal to its planar surface a cylindrical magnetizable member 51 which acts as a flux concentrator and mounting post which fit snuggly into the apertures 51A provided on guide member 42. The sensing axis of each cell 46 – 48 is substantially aligned with the diameter of the base of its cylindrical post 51 in a symmetrical manner about the post's center. Concentrically aligned with apertures 51A are larger clearance holes 52 provided in the member 14 for clearance of posts 51 of cells 47, 48. Keyhole aperture 20 provides this same function for the post 51 of cell 46. Compatibly aligned holes 53 are provided on the members 42 and 14 through which are fed the insulated multiwire conductor cables 54, partially shown in FIG. 1, connected to the cells 47, 48, respectively. Each cable 54 contains the required amount of input and output conductors associated with the particular Hall cell. The corresponding cable 54 associated with cell 46 is fed through hole 53A of member 42 and aperture 20 of member 14. In this manner interconnection to the cables 54 by the associated power and sensor circuitry is made at the rear of plate member 14 and away from the moving parts of the apparatus mounted on the front and/or sides of plate member 14. Preferably, apparatus 1 is made of non-magnetizable material, e.g., aluminum, so that it will not affect the action of Hall cells 46 - 48 and associated actuating magnets 49, 50. Moreover, since the respective sense axis of cells 46 – 48 are symmetrically aligned with the diameter and about the center of the respective posts 51, angular misorientation of the particular cell about the central longitudinal axis of its post 51 when mounted in its associated aperture 51A does not adversely effect the cell's sensitivity.

The various components may be judiciously mounted on each side of the frame member 14 so that assembly 1 is substantially counterbalanced. In addition, the stand 15 may be mounted to a suitable base, shown schematically in FIG. 1 and designated by the reference number 55, for sake of simplicity.

The preferred operational mode of apparatus 1 will next be described. For purposes of explanation, it will be assumed that block 8 is at rest and located along chain reach 6 so that the object 2 is located at X position coordinate X1 and a predetermined Y coordinate, e.g., Y0. For this condition, driver 12, and more particularly, motor 13 and, hence, chain 5 are likewise at rest. It is assumed further, that it is now desired to transfer object 2 to the other X coordinate X2 and a predetermined Y coordinate, e.g., +Y1.

In response to a suitable start signal, motor 13 is actuated in the clockwise direction, c.f., arrow CW in FIG. 1, causing sprocket wheel 4 to rotate. As a result, chain 5 begins to rotate in a corresponding clockwise direction. In response to the movement of chain 5, block 8 is carried in an upward direction. The upward movement of the block 8 is transferred to the bars 30, 31 of means 9 and in turn is imparted to the U-shaped member 10. Object 2 is thus withdrawn upwardly in an accurate aligned manner along the X1 coordinate in a precise and controlled manner by the restraining effects of the guide means 11. At the same time, object 2 is prevented from being translated in the X direction by the restraining forces exerted by the chain guide means 40 - 42.

As the particular link to which the block 8 is connected becomes entrained on the teeth of the sprocket wheel 3, a component force in the X direction is transmitted through the pin 5A causing block 8 to move in the X direction towards the right as viewed facing FIG. 1 concurrently with the movement of block 8 in its upward direction. The X component of the force so exerted, overcomes the aforedescribed restraining forces causing the bars 30, 31 to also move towards the right. After the pin 5A reaches the top dead center of sprocket wheel 3, the X component of the forces continues to be generated in a direction towards the right, but the Y component force is now in the reverse, i.e., downward, direction. The magnet 49 carried by the block 8 passes the Hall cell 46 actuating the latter so that a resultant control signal is generated therefrom which is indicative of the distance of the object 2 form a given Y reference position, e.g., Y0. This control signal is used to index the stepper motor 13 so that it will position the object to the desired Y coordinate, +Y1, at which point the movements of the driver means 12, motor 13 and chain 5 are terminated.

Thus, as the link to which the block 8 is connected becomes disengaged from the sprocket wheel 3 as the chain 5 is being driven clockwise, motion in the X direction of the block 8 towards the right terminates but the block 8 continues in the downward direction. Once again, the guide means 11 maintains the means 10 and, consequently, object 2 accurately aligned along the X2 coordinate in the Y direction and the aforedescribed restraining forces prevent the bars 30, 31 from moving in the X direction. The resultant control signal generated by Hall cell 46 in response to the actuating magnet 49, causes motor 13 to index object 2 to the desired position +Y1.

In the preferred operational mode, a similar operation occurs when it is desired to return object 2 to the X1 coordinate and a desired Y coordinate at that location by reversing the direction of the motor 13. Hall cell 46 senses the acting magnet 49 and a resultant output signal is generated therefrom which is indicative of the distance of the object 2 from the desired Y coordinate along the X1 coordinate or location. Hall cells 47 and 48 detect when the block 8 and, consequently, object 2 are at some predetermined Y axis limit position −Ymin along the X1 and X2 coordinates, respectively. Control means for controlling the operation of the stepper motor 13 so that the chain 5 causes the object 2 to be indexed to the desired Y coordinate are generally well-known to those familiar with the art. Hence, they have been omitted herein for sake of clarity, as they are not necessary for an understanding of the present invention.

Figure 5:
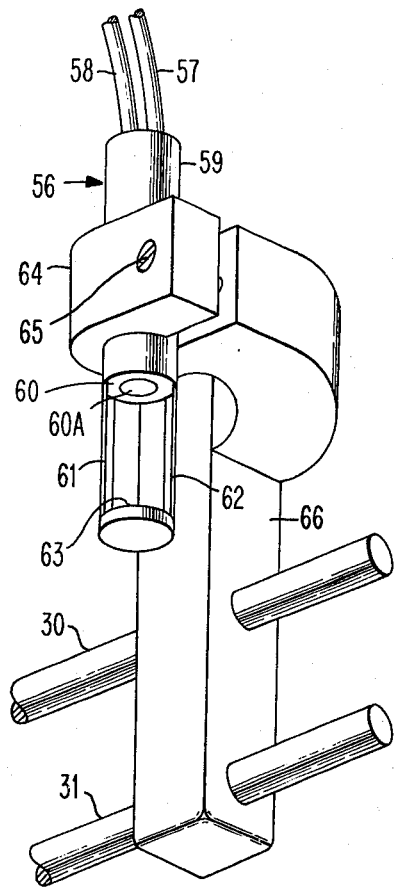
FIG. 5 is an enlarged partial perspective view of an embodiment of an object which is positioned by the apparatus of FIG. 1.

Referring now to FIG. 5, there is shown a preferred embodiment of the object 2 that is positioned by the apparatus of FIG. 1. In this embodiment, object 2 is a fiber optic test probe 56 which includes a pair of fiber optic cables 57, 58 that are fitted to a demountable adapter 59. Cables 57, 58 have a bifurcated end 60A which is exposed at the end 60 of adapter 59. Suspended from adapter 59 by a pair of integrally-formed elongated brackets 61, 62 and in facing relationship with the exposed bifurcated end 60A of cables 57, 58 is a reflector 63. The cylindrical-shaped adapter 59 is inserted into a clamp member 64 which has a securing screw 65 that when secured causes the adapter 59 to be firmly held within the member 64. The member 64 has an elongated portion 66 which is adjustably secured to the object support bars 30, 31 of apparatus 1.

In operation, the fiber optic probe 56 of FIG. 5 is immersed by the apparatus of FIG. 1 in a fluid sample or specimen, not shown, carried in a cell such as a test tube or the like, not shown. As a result, fluid passes through the two openings formed between brackets 61, 62, thus providing a fixed uniform volume of the sample proportinal to the distance between the end 60 and reflector 63. Light is projected into the nonimmersed input end, not shown, of cable 57 from where it is transmitted by the cable 57 and emerges out of the bifurcated end 60A associated with the end face 60 of adapter 59. The emitted light passes through the sample and is reflected by reflector 63 back through the sample and into the bifurcated end 60A of the cable pair 57, 58. The reflected light picked up by the cable 58 is then transmitted to and out of its non-immersed output end, not shown, where it is subsequently analyzed by suitable means such as a photospectrophotometer as the one described in copending application, Ser. No. 587,459, filed June 16, 1975, and entitled "Self-Calibratable Spectrum Analyzer," Ralph N. Jackson, Richard W. Kern, and Alvin H. Tong, and assigned to the common assignee hereof.

Figure 6:
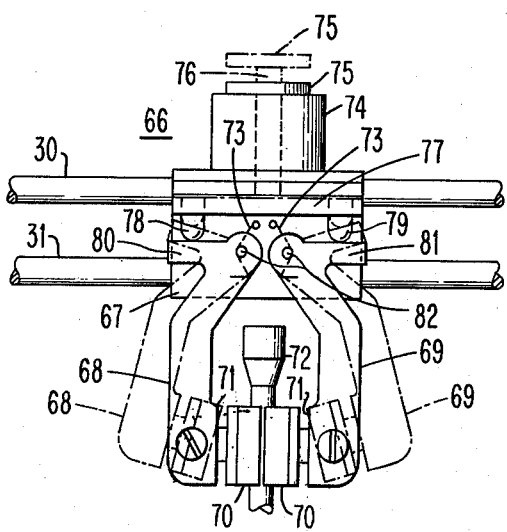
FIG. 6 is a partial perspective view of still another embodiment of an object which is positioned by the apparatus of FIG. 1.

In the embodiment of FIG. 6, object 2 is a gripper mechanism generally indicated by the reference numeral 66. The mechanism 66 is supported on a support block 67 which is adjustable secured to the object bars 30, 31 of apparatus 1. The gripper mechanism is described in the publication entitled "Gripper Mechanism" by J. L. Sirico, co-inventor herein, IBM Technical Disclosure Bulletin, Vol. 17, No. 8, January 1975, page 2246. Briefly, it includes a pair of pivotable jaws 68, 69. A set of replaceable resilient grips 70 are provided at the respective jaw faces 71. In the embodiment of FIG. 6, a gripper mechanism 67 is used to grip cylindrical objects such as, for example, partially shown test tube 72. The jaws 68, 69 are normally biased to an open position, as shown in their dash-dot outlined form in FIG. 6 by suitable torsion springs 73 shown schematically in FIG. 6 for sake of clarity. To close the jaws 68, 69, a solenoid 74 is energized causing the attraction of its armature 75, which is attached to the stem member 76, to go from its normally unretracted position, as shown in its phantom dash-dot outline form in FIG. 6, to its retracted position shown in solid form therein. The armature 75 is attached to a cam plate 77 by the stem 76. The cam plate 77 carries two cam elements 78, 79. The cam elements 78, 79 engage the upper crank-like ends 80, 81, respectively, of the jaws 68, 69 so that when the solenoid 74 is energized, the armature 75 and cam plate 77 move downwardly thereby causing the ends 80, 83 to pivot the jaw members 68, 69 about their respective pivots 82 and thus, placing the jaws 68 and 69 in the closed position, as shown in their solid form in FIG. 6.

The operation of the respective object means 2 of FIGS. 5 and 6 are synchronized with the operation of apparatus 1.

As is obvious to those skilled in the art, while the invention has been described with a particular structural configuration, orientation, object types, and mode of operation, it is to be understood that the invention may be practiced with other configurations, orientations, object types, and/or operational modes as is apparent to those skilled in the art. Thus, for example, the apparatus of FIG. 1 can be oriented horizontally in lieu of the vertical orientation shown therein. Moreover, the apparatus of FIG. 1 can be modified to have an asymmetrical configuration in lieu of the symmetrical one shown therein. Likewise, the operation of the chain 5 can be modified to be unidirectional. If desired, the orientation of the elongated axis of object support mean 9 with respect to the elongated axis of guide means 11 and, hence, with respect to the orientation of reaches 6, 7 can be modified from the orthogonal relationship shown in FIG. 1 to other angular orientation having different angles of skew. Moreover, the apparatus of FIG. 1 can position other types of objects, such as mechanical or electromechanical probes, or workpieces such as a drill or drill bit and the like, etc.

Thus, while the invention has been particularly shown and described with reference to preferred embodiments thereof, it will be understood by those skilled in the art that various changes in form and details may be made therein without departing from the spirit and scope of the invention.

We claim:

1. Apparatus for positioning an object to two spatially displaced first and second positions, said apparatus comprising:
   first and second rotatable sprocket wheels disposed in a common plane,
   an endless sprocket chain entrained about said sprocket wheels in operable relationship therewith, said chain having first and second opposing reaches between said wheels,
   first member means pivotably connected to said chain,
   second member means affixed to said first member means and adapted to support said object,
   third member means having said second member means slidably mounted thereto,
   guide member means for guiding said third member means in a predetermined aligned relationship with said reaches,
   chain guide means for guiding said chain along said first and second reaches, and
   driver means coupled to one of said wheels for driving said endless chain to carry said first member means along each of said first and second reaches, said object being positionable thereby with respect to said first position when said chain carries said first member means along said first reach, and said object being positionable thereby with respect to said second position when said chain carries said first member means along said second reach.

2. Apparatus according to claim 1 wherein said chain is reversibly operable by said driver means and said one of said wheels.

3. Apparatus according to claim 1 wherein said driver means comprises a stepper motor.

4. Apparatus according to claim 1 wherein said object comprises article gripper means.

5. Apparatus according to claim 1 wherein said object comprises predetermined probe means.

6. Apparatus according to claim 5 wherein said probe means comprises a fiber optic probe.

7. Apparatus for positioning an object to two spatially displaced first and second positions, said apparatus comprising:
   frame member means,
   first and second sprocket wheels rotatably mounted on said frame means in a common plane,
   an endless sprocket chain entrained about said sprocket wheels in operable relationship therewith, said chain having first and second substantially parallel reaches between said wheels,
   first member means pivotably connected to said chain,
   second member means affixed to said first member means and adapted to support said object,
   first guide member means having said second member means reciprocably slidably mounted thereto along a predetermined first direction,
   second guide member means for guiding said first guide member means in parallel relationship with said reaches,
   chain third guide means for guiding said chain along said first and second reaches, and
   driver means coupled to one of said wheels for driving said endless chain to carry said first member means along each of said first and second reaches, said object being positionable thereby with respect to said first position when said chain carries said first member means along said first reach, and said object being positionable thereby with respect to said second position when said chain carries said first member means along said second reach.

8. Apparatus according to claim 7 wherein said chain is reversibly operable by said driver means and said one of said wheels.

9. Apparatus according to claim 7 wherein said driver means comprises a stepper motor, said stepper motor selectively indexing said chain to cause corresponding indexing of said object with respect to each of said first and second positions.

10. Apparatus according to claim 7 wherein said object comprises article gripper means.

11. Apparatus according to claim 7 wherein said object comprises predetermined probe means.

12. Apparatus according to claim 11 wherein said probe means comprises a fiber optic probe.

13. Apparatus according to claim 7 wherein said predetermined first direction is substantially orthogonal to said parallel reaches.

14. Apparatus for positioning an object with respect to first and second lateral positions located along first and second predetermined X coordinates of a predetermined XY reference plane, said apparatus comprising:
   frame member means,
   first and second chain sprocket wheels rotatably mounted on said frame means in a common plane, said common plane being in coplanar relationship with said reference plane, and each of said wheels having a diameter substantially equal to the distance between said first and second positions,
   an endless sprocket chain entrained about said sprocket wheels in operable relationship therewith, said chain having first and second substantially elongated parallel reaches between said wheels, said reaches being in parallel relationship with the X axis of said reference plane,
   blocklike first member means pivotably connected to said chain,
   second member means having at least one elongated bar affixed to said first member means adapted to support said object,
   first guide member means having said at least one elongated object support bar reciprocably slidably mounted thereto along a predetermined first direction,
   second guide means including at least one elongated said member mounted to said frame member means in parallel relationship with said first and second chain reaches, said first guide means being adapted to be guided along said at least one elongated rail member,
   chain third guide means having a pair or elongated rail guides disposed along each side of each of the chain reaches, and
   driver means coupled to one of said wheels for driving said endless chain to carry said first member means along each of said first and second reaches, said object being positionable thereby with respect to said first position when said chain carries said first member means along said first reach, and said object being positionable thereby with respect to said second position when said chain carries said first member means along said second reach.

15. Apparatus according to claim 14 wherein said chain is reversibly operable by said driver means and said one of said wheels.

16. Apparatus according to claim 14 wherein said driver means includes a reversibly operable stepper motor, said stepper motor selectively indexing said chain to cause corresponding indexing of said object with respect to each of said first and second positions.

17. Apparatus according to claim 16 wherein said predetermined first direction is substantially orthogonal to said parallel reaches, and said stepper motor causes said object to be selectively indexable along the Y direction at each of said first and second X coordinates.

18. Apparatus according to claim 14 wherein said object comprises article gripper means.

19. Apparatus according to claim 14 wherein said object comprises test tube gripper means.

20. Apparatus according to claim 14 wherein said object comprises a fiber optic probe.

21. Apparatus according to claim 14 further comprising stationary sensor means and actuator means for actuating said sensor means, said actuator means being carried by said first member means, said sensor means providing at least one output signal in response to said actuator means indicative of the relative position and direction of movement of said object with respect to a predetermined reference position.

* * * * *